(12) United States Patent
Zook et al.

(10) Patent No.: US 9,987,362 B2
(45) Date of Patent: Jun. 5, 2018

(54) HYDROGEL FORMULATION WITH MILD ADHESION

(71) Applicant: ZOETIS SERVICES LLC, Florham Park, NJ (US)

(72) Inventors: Christopher A. Zook, Kalamazoo, MI (US); Michael T. Sweeney, Portage, MI (US); Rebecca R. Quesnell, Kalamazoo, MI (US); Fiona Patricia Clements, Stone Mountain, GA (US); Claude-Raymond René, Atlanta, GA (US); Bruktawit Asfaw, Mableton, GA (US); Sarah Barbara Kokotoff, Dunwoody, GA (US); Dominic Dominicovich Ugbedah, Lawrenceville, GA (US)

(73) Assignee: Zoetis Services LLC, Florham Park, NJ (US)

( * ) Notice: Subject to any disclaimer, the term of this patent is extended or adjusted under 35 U.S.C. 154(b) by 0 days. days.

(21) Appl. No.: 15/147,530

(22) Filed: May 5, 2016

(65) Prior Publication Data
US 2016/0324969 A1    Nov. 10, 2016

Related U.S. Application Data

(60) Provisional application No. 62/157,627, filed on May 6, 2015.

(51) Int. Cl.
| A61K 47/32 | (2006.01) |
| A61K 9/00 | (2006.01) |
| A61K 45/06 | (2006.01) |
| A61K 9/06 | (2006.01) |
| A61K 31/546 | (2006.01) |
| A61K 31/745 | (2006.01) |

(52) U.S. Cl.
CPC ............ *A61K 47/32* (2013.01); *A61K 9/0017* (2013.01); *A61K 9/06* (2013.01); *A61K 31/546* (2013.01); *A61K 31/745* (2013.01); *A61K 45/06* (2013.01)

(58) Field of Classification Search
CPC ... A01N 59/00; Y10S 514/887; A61K 31/546; A61K 31/745; A61K 45/06; A61K 47/32
See application file for complete search history.

(56) References Cited

U.S. PATENT DOCUMENTS

| 4,113,854 A | 9/1978 | Andrews et al. |
| 4,434,181 A | 2/1984 | Marks, Sr. et al. |
| 5,017,369 A * | 5/1991 | Marhevka ............ A61K 9/0041 424/407 |
| 5,203,812 A | 4/1993 | Eckold et al. |
| 5,508,317 A | 4/1996 | Müller |
| 5,583,163 A | 12/1996 | Müller |
| 5,665,840 A | 9/1997 | Pöhlmann et al. |
| 5,807,927 A | 9/1998 | Stockinger et al. |
| 5,819,988 A | 10/1998 | Sawhney et al. |
| 5,849,841 A | 12/1998 | Mühlebach et al. |
| 5,932,674 A | 8/1999 | Müller |
| 5,939,489 A | 8/1999 | Müller |
| 5,989,215 A | 11/1999 | Delmotte et al. |
| 6,011,077 A | 1/2000 | Müller |
| 6,395,289 B1 | 5/2002 | Ehrhard et al. |
| 6,652,883 B2 | 11/2003 | Goupil et al. |
| 7,666,339 B2 | 2/2010 | Chaouk et al. |
| 8,353,877 B2 | 1/2013 | Hallahan et al. |
| 2001/0036451 A1 | 11/2001 | Goupil et al. |
| 2002/0122771 A1 | 9/2002 | Holland et al. |
| 2003/0134032 A1 | 7/2003 | Chaouk et al. |
| 2005/0191270 A1 * | 9/2005 | Gruening ............. A61K 9/0019 424/78.3 |
| 2006/0073216 A1 * | 4/2006 | McNaughton ..... A61K 31/4166 424/661 |
| 2007/0093907 A1 | 4/2007 | Goupil et al. |
| 2007/0249712 A1 | 10/2007 | Dee et al. |
| 2008/0305149 A1 | 12/2008 | Hirt et al. |
| 2009/0149954 A1 | 6/2009 | Hu et al. |
| 2009/0253650 A1 | 10/2009 | Pongsamart et al. |
| 2009/0281063 A1 * | 11/2009 | Inagi ................... A61K 9/0009 514/90 |
| 2012/0009275 A1 * | 1/2012 | Asfaw ................... A01N 25/04 424/619 |
| 2012/0301407 A1 | 11/2012 | Durham et al. |
| 2015/0080841 A1 | 3/2015 | Bradley et al. |

FOREIGN PATENT DOCUMENTS

| CN | 103275351 | 9/2013 |
| WO | WO 97/21497 | 6/1997 |
| WO | WO 03/022245 | 3/2003 |
| WO | WO 2013/021186 | 2/2013 |
| WO | WO 2015/038281 | 3/2015 |

OTHER PUBLICATIONS

Klemm et al (Applied Microbiology and Biotechnology, 2010, vol. 88, pp. 451-459).*
Schukken et al (Journal of Dairy Science, 2011, vol. 94, pp. 6203-6215).*

* cited by examiner

*Primary Examiner* — Mark V Stevens
(74) *Attorney, Agent, or Firm* — Womble Bond Dickinson (US) LLP

(57) ABSTRACT

The present disclosure relates to methods, compositions, and devices for treatments related to mammary tissue in subjects, including reducing the incidence of mastitis. In particular, the disclosure can relate to creating a physical barrier on a teat surface, in a teat canal, or in a teat cistern for prophylactic treatment of mammary disorders.

27 Claims, 3 Drawing Sheets

HYDROGEL FORMULATION WITH MILD ADHESION

CROSS-REFERENCE TO RELATED APPLICATIONS

The present application claims priority to U.S. Provisional Pat. App. No. 62/157,627, filed May 6, 2015, the disclosure of which is incorporated herein by reference.

FIELD OF THE INVENTION

The present invention is generally in the field of compositions having mild adhesion and medical and health related uses of such compositions. The invention is also in the field of methods, compositions, and devices for protecting the udder from pathogenic load and the resultant decrease in the incidence of mastitis in an animal. In one embodiment, the invention is methods, compositions, and devices for creating a physical barrier on the teat and udder surface or in the teat canal of an animal for prevention and/or treatment of mammary disorders. In one embodiment, the methods and compositions are designed for use in mid- to late-gestation and during the animal's dry period. In one embodiment, the methods and compositions are designed for placement in the teat cistern. In one embodiment, the methods and compositions are designed for placement in adhering to the external teat.

BACKGROUND OF THE INVENTION

Mastitis is an inflammation of the mammary gland that is caused by bacteria which in most cases enter the gland via the teat orifice. During the non-lactating period or "dry period" in the gland, deposits of keratin in the teat orifice and the streak canal form a primary defense mechanism. A keratin plug that forms in the teat of the animal forms a protective barrier, and the immune-rich tissues of the Furstenbürg's Rosette in the teat, as well as the natural protective factors of the dry-cow secretions, contain high levels of naturally occurring anti-bacterial substances which inhibit the passage of bacteria from the teat orifice to the teat cistern (papillary sinus) and gland cistern. However, this keratin plug and these natural immune defense mechanisms are often overcome by bacterial invasion as the animal is transitioning to the dry period, during the dry period of the animal, and/or during calving. This can result in bacteria invading the gland and causing mastitis during the dry period or, more particularly, immediately following calving.

Products have been developed to seal an animal's teat to prevent mastitis and other conditions. Barrier teat dips are designed for extra-mammary use, to seal the external surface and streak canal of the teat, and are typically used during periods of milking. For heifers, external dip products exist, but none sufficiently seal the teat of the cow externally for a sufficient amount of time to prevent the unique form of mastitis that is so dangerous in heifers. In some heifers and in cows that have experienced one or more pregnancies previously, teat sealants are also used to block or seal the teat canal during the dry period. Furthermore teat sealants are used to plug the teat cistern during the dry period.

U.S. Pat. Nos. 6,395,289 and 6,203,812 to Hydromer teach hydrophilic polymeric blends for use as teat dips during the lactating period. The blends provide barrier properties but can be rapidly removed prior to milking. However, the physical consistency and properties of these teat dips make them unsuitable for teat canal or cistern placement. For example, since these dips do not gel readily, they would tend to not remain in the canal or cistern.

Other teat dip compositions used during an animal's lactating period are disclosed in U.S. Pat. Nos. 4,113,854 and 5,017,369. Applied externally, these compositions form thick films which seal off the end of a teat canal. These compositions include latex and remain viscous and sticky thereby not allowing for teat canal protection from the environmental factors to which the gland is naturally exposed due to its location on the animal. Also, latex may be toxic or irritating to the mammary gland tissues. In addition to the contamination of milk, latex can elicit allergic reactions in humans.

U.S. Pat. No. 5,583,163 to Ciba Geigy and U.S. Pat. No. 5,932,674 to Novartis AG describe methods for the preparation of certain polyvinyl alcohol (PVA) polymers and hydrogels. U.S. Pat. No. 6,652,883 to BioCure teaches the use of PVA based hydrogels as bulking and sealing products. However, the formulations taught in the '883 patent do not have appropriate properties to be useful as intra-canal or intra-teat cistern sealants.

What is needed is a safe formulation that is easy and safe to apply and that preferably forms in place on the tissue. The formed hydrogel has mild adhesion, in the range of 0.05 to 0.5N.

SUMMARY OF THE INVENTION

In one aspect, the invention is a hydrogel composition suitable for use, for example, as an animal teat sealant formed from macromers. The macromers can be in situ polymerized into the hydrogel teat sealant directly on or in an animal teat. In a preferred embodiment, the hydrogel composition is formed from a two part sterile liquid composition; one or both of the parts can contain the macromer, which are delivered to the teat in either a spray, dip, stream or infusion manner, whereupon they combine and polymerize immediately to form the hydrogel. Optionally, active agents such as antimicrobial agents, analgesics, or anti-inflammatories may be included.

By rapidly forming the hydrogel when applied, the method of forming a teat sealant is fast, clean, "touchless" (hands free), and simple. Because it forms in situ, the sealant is highly conformal to the teat interior or exterior surface which ensures a better seal against infection and that any included active agents are more efficiently delivered directly to the teat.

The macromer is a water soluble synthetic polymer made by functionalizing a water soluble polyvinyl alcohol (PVA). PVA macromer in water may be unstable under certain sterilization and storage conditions. The composition thus may include means to stabilize the compositions prior to application. The PVA macromer is optimized by molecular weight, acetate content, and functional group content. These factors significantly affect viscosity, water uptake ability, hydrogel forming rate, adhesion, and mechanical properties of the hydrogel. A pure PVA hydrogel tends to dry out over a few hours, and this drying leads to a significant shrinkage and property changes of the hydrogel. Therefore, the composition may also contain moisturizers. In addition, thickening agents or density modifiers may be added to provide weight to the hydrogel to facilitate ease of use.

The macromers can be crosslinked through any appropriate means (such as application of ultraviolet light) but are preferably crosslinked using a $H_2O_2/Fe(II)$ redox free radical initiation system. The reducing agent and oxidizing agent are separately packaged in the two composition parts, either or both of which can contain macromer.

The hydrogel has the qualities necessary to serve for many medical-related functions, including as a teat sealant. In particular the hydrogel has appropriate adhesion, swelling, and the mechanical strength allowing it to stay in place for an indefinite period of time.

In another embodiment, the teat sealant is a preformed infused hydrogel. In another embodiment, the teat sealant hydrogel forms an external cover on the teat.

In another aspect, the present invention provides methods of preventing or treating mastitis in an animal, comprising administering about 0.5 to about 5.0 g of a Hydrogel Composition, as defined below, per teat to the animal.

The present invention provides methods of preventing or treating an internal microbial infection in an animal, comprising administering about 0.5 to about 5.0 g of a Hydrogel Composition to the animal. More particularly, the present invention provides such methods wherein the internal microbial infection is mastitis.

The present invention provides methods of eliminating a bacterial invasion in an animal, comprising administering about 0.5 to about 5.0 g of a Hydrogel Composition to the animal.

Even more particularly, the present invention provides the above methods wherein about 1.0 to about 4.0 g of Hydrogel Composition is administered. Also, the invention provides such methods wherein the animal is a livestock animal, more particularly heifers or cows. Also, the invention provides such methods wherein the Hydrogel Composition is administered during the transition period through the dry period of the heifer or cow. Also, the invention provides such methods wherein an antimicrobial agent is also administered to the animal, such as ceftiofur hydrochloride. Also, the present invention provides such methods wherein the composition is administered to the animal by infusion into the teat of the animal or where the composition is administered to the animal by external application to the teat of the animal. Most particularly, the present invention provides such methods wherein the composition is Formulation A4, I or I4 as disclosed herein.

The present invention provides methods of forming a physical barrier in the teat canal of an animal for prophylactic treatment of mammary disorders during the animal's transition period through dry period, comprising the step of infusing a Hydrogel Composition into the teat cistern of the animal. More particularly, the present invention provides such methods, wherein the treatment includes controlling invasion of the mammary gland by a mastitis-causing organism.

The present invention provides methods of forming a physical barrier in the teat canal of an animal for prophylactic treatment of mammary disorders during the animal's transition period through dry period, comprising the step of externally applying a Hydrogel Composition to the teat of the animal. More particularly, the present invention provides methods wherein the treatment includes controlling invasion of the mammary gland by a mastitis-causing organism.

The present invention provides systems for forming a physical barrier in the teat canal of an animal for the prophylactic treatment of mammary disorders during the animal's transition period through dry period, said system comprising a Hydrogel Composition and an injection device for infusing the composition into the teat cistern of the animal. More particularly, the present invention provides such systems wherein the treatment includes controlling invasion of the mammary gland by a mastitis-causing organism. More particularly, the present invention provides such systems wherein the Hydrogel Composition is infused during the transition period through the dry period of the heifer or cow.

In another aspect, the present invention provides methods for combatting microbial mammary mastitis in an animal which method permits milk obtained from the animal to be used in the production of a milk product, the method comprising administering to the animal a Hydrogel Composition. More particularly, the invention provides methods wherein the Hydrogel Composition is administered prior to infection of a healthy animal.

In another aspect, the present invention provides methods for reducing the withholding time of milk obtained from an animal being treated for mastitis for the production of a milk product, wherein the Hydrogel Composition is administered to the animal. The present invention also provides methods for reducing the withholding time of milk obtained from an animal being prophylactically treated for mastitis for the production of a milk product, wherein a Hydrogel Composition is administered to the animal.

Even more particularly, the present invention provides the above methods wherein the milk product is milk, yogurt or cheese. Even more particularly, the invention provides such methods wherein the milk is dry or fluid milk. Also, the present invention provides such methods wherein the Hydrogel Composition is administered via intramammary infusion or by dipping the teat. Also, the present invention provides such methods wherein the animal is a heifer or cow and wherein the administration is achieved by intramammary infusion during the transition period or the dry period. Also the present invention provides such methods wherein the Hydrogel Composition is administered during the postpartum period of a non-lactating animal or wherein the Hydrogel Composition is administered during the prepartum period of an animal.

The present invention thus provides methods of using a Hydrogel Composition as a teat sealant in an animal in need thereof. It also provides uses of a Hydrogel Composition in the manufacture of a medicament for the prevention or treatment of a microbial infection in an animal, such as mastitis.

Further to the above, the present invention may be defined in particular by any one or more of the following embodiments.

Embodiment 1

A method of preventing or treating mastitis in an animal, comprising administering about 0.5 to about 5.0 g of a Hydrogel Composition per teat to the animal.

Embodiment 2

The method of Embodiment 1, wherein about 1.0 to about 4.0 g of Hydrogel Composition is administered.

Embodiment 3

The method of Embodiment 1, wherein the animal is a livestock animal.

Embodiment 4

The method of Embodiment 3, wherein the livestock animal is a heifer or cow.

Embodiment 5

The method of Embodiment 1, wherein the Hydrogel Composition is administered during the transition period through the dry period of the heifer or cow.

Embodiment 6

The method of Embodiment 1, wherein Hydrogel Composition is a polymerizing hydrogel.

Embodiment 7

The method of Embodiment 1, wherein an antimicrobial agent is also administered to the animal.

Embodiment 8

The method of Embodiment 7, wherein the antimicrobial agent is ceftiofur hydrochloride.

Embodiment 9

The method of Embodiment 1, wherein the composition is administered to the animal by infusion into the teat of the animal.

Embodiment 10

The method of Embodiment 1, where the composition is administered to the animal by external application to the teat of the animal.

Embodiment 11

The method of Embodiment 1, wherein the composition is Formulation A4, I or I4 as disclosed herein.

Embodiment 12

A method of preventing or treating an internal microbial infection in an animal, comprising administering about 0.5 to about 5.0 g of a Hydrogel Composition to the animal.

Embodiment 13

The method of Embodiment 12, wherein the internal microbial infection is mastitis.

Embodiment 14

The method of Embodiment 12, wherein about 1.0 to about 4.0 g of a Hydrogel Composition is administered.

Embodiment 15

The method of Embodiment 12, wherein the animal is a livestock animal.

Embodiment 16

The method of Embodiment 15, wherein the livestock animal is a heifer or cow.

Embodiment 17

The method of Embodiment 12, wherein the Hydrogel Composition is administered during the transition period through the dry period of the heifer or cow.

Embodiment 18

The method of Embodiment 12, wherein the Hydrogel Composition is a polymerizing hydrogel.

Embodiment 19

The method of Embodiment 12, wherein an antimicrobial agent is also administered to the animal.

Embodiment 20

The method of Embodiment 19, wherein the antimicrobial agent is ceftiofur hydrochloride.

Embodiment 21

The method of Embodiment 12, wherein the composition is administered to the animal by infusion into the teat of the animal.

Embodiment 22

The method of Embodiment 12, where the composition is administered to the animal by external application to the teat of the animal.

Embodiment 23

The method of Embodiment 12, wherein the composition is Formulation A4, I or I4 as disclosed herein.

Embodiment 24

A method of eliminating a bacterial invasion in an animal, comprising administering about 0.5 to about 5.0 g of a Hydrogel Composition to the animal.

Embodiment 25

The method of Embodiment 24, wherein about 1.0 to about 4.0 g of the Hydrogel Composition is administered.

Embodiment 26

The method of Embodiment 24, wherein the animal is a livestock animal.

Embodiment 27

The method of Embodiment 26, wherein the livestock animal is a heifer or cow.

Embodiment 28

The method of Embodiment 24, wherein the Hydrogel Composition is administered during the transition period through the dry period of the heifer or cow.

Embodiment 29

The method of Embodiment 24, wherein the Hydrogel Composition is a polymerizing hydrogel.

Embodiment 30

The method of Embodiment 24, wherein an antimicrobial agent is also administered to the animal.

Embodiment 31

The method of Embodiment 30, wherein the antimicrobial agent is ceftiofur hydrochloride.

Embodiment 32

The method of Embodiment 24, wherein the composition is administered to the animal by infusion into the teat of the animal.

Embodiment 33

The method of Embodiment 24, where the composition is administered to the animal by external application to the teat of the animal.

Embodiment 34

The method of Embodiment 24, wherein the composition is Formulation A, A4, I or I4 as disclosed herein.

Embodiment 35

A method of forming a physical barrier in the teat canal of an animal for prophylactic treatment of mammary disorders during the animal's transition period through dry period, comprising the step of infusing a Hydrogel Composition into the teat cistern of the animal.

Embodiment 36

The method of Embodiment 35, wherein the treatment includes controlling invasion of the mammary gland by a mastitis-causing organism.

Embodiment 37

The method of Embodiment 36, wherein the mammary disorder is mastitis.

Embodiment 38

The method of Embodiment 35, wherein about 0.5 to about 5.0 g of the Hydrogel Composition is infused per teat cistern to the animal.

Embodiment 39

The method of Embodiment 38, wherein about 1.0 to about 4.0 g of a Composition according to the present disclosure is infused per teat cistern to the animal.

Embodiment 40

The method of Embodiment 35, wherein the animal is a livestock animal.

Embodiment 41

The method of Embodiment 40, wherein the livestock animal is a heifer or cow.

Embodiment 42

The method of Embodiment 35, wherein the Hydrogel Composition is infused during the transition period through the dry period of the heifer or cow.

Embodiment 43

The method of Embodiment 35, wherein the Hydrogel Composition is a polymerizing hydrogel.

Embodiment 44

The method of Embodiment 35, wherein an antimicrobial agent is also infused into the teat cistern of the animal.

Embodiment 45

The method of Embodiment 44, wherein the antimicrobial agent is ceftiofur hydrochloride.

Embodiment 46

The method of Embodiment 35, wherein the composition is Formulation A4, I or I4 as disclosed herein.

Embodiment 47

A method of forming a physical barrier in the teat canal of an animal for prophylactic treatment of mammary disorders during the animal's transition period through dry period, comprising the step of externally applying a Hydrogel Composition to the teat of the animal.

Embodiment 48

The method of Embodiment 47, wherein the treatment includes controlling invasion of the mammary gland by a mastitis-causing organism.

Embodiment 49

The method of Embodiment 48, wherein the mammary disorder is mastitis.

Embodiment 50

The method of Embodiment 47, wherein about 0.5 to about 5.0 g of the Hydrogel Composition is applied per teat to the animal.

Embodiment 51

The method of Embodiment 50, wherein about 1.0 to about 4.0 g of the Hydrogel Composition is applied.

Embodiment 52

The method of Embodiment 47, wherein the animal is a livestock animal.

Embodiment 53

The method of Embodiment 52, wherein the livestock animal is a heifer or cow.

Embodiment 54

The method of Embodiment 47, wherein the Hydrogel Composition is applied during the transition period through the dry period of the heifer or cow.

Embodiment 55

The method of Embodiment 47, wherein the Hydrogel Composition is a polymerizing hydrogel.

Embodiment 56

The method of Embodiment 47, wherein an antimicrobial agent is also administered to the animal.

Embodiment 57

The method of Embodiment 56, wherein the antimicrobial agent is ceftiofur hydrochloride.

Embodiment 58

The method of Embodiment 47, wherein the composition is Formulation A4, I or I4 as disclosed herein.

Embodiment 59

A system for forming a physical barrier in the teat canal of an animal for the prophylactic treatment of mammary disorders during the animal's transition period through dry period, said system comprising a Hydrogel Composition and an injection device for infusing the composition into the teat cistern of the animal.

Embodiment 60

The system of Embodiment 56, wherein the treatment includes controlling invasion of the mammary gland by a mastitis-causing organism.

Embodiment 61

The system of Embodiment 57, wherein the mammary disorder is mastitis.

Embodiment 62

The system of Embodiment 56, wherein about 0.5 to about 5.0 g of the Hydrogel Composition is infused per teat cistern to the animal.

Embodiment 63

The system of Embodiment 59, wherein about 1.0 to about 4.0 g of the Hydrogel Composition is infused per teat cistern to the animal.

Embodiment 64

The system of Embodiment 56, wherein the animal is a livestock animal.

Embodiment 65

The system of Embodiment 61, wherein the livestock animal is a heifer or cow.

Embodiment 66

The system of Embodiment 56, wherein the Hydrogel Composition is infused during the transition period through the dry period of the heifer or cow.

Embodiment 67

The system of Embodiment 56, wherein Composition X is a polymerizing hydrogel.

Embodiment 68

The system of Embodiment 56, wherein an antimicrobial agent is also infused into the teat cistern of the animal.

Embodiment 69

The system of Embodiment 65, wherein the antimicrobial agent is ceftiofur hydrochloride.

Embodiment 70

The system of Embodiment 59, wherein the composition is Formulation A4, I or I4 as disclosed herein.

Embodiment 71

A method for combatting microbial mammary mastitis in an animal which method permits milk obtained from the animal to be used in the production of a milk product, the method comprising administering to the animal a Hydrogel Composition.

Embodiment 72

The method of Embodiment 71, wherein about 0.5 to about 5.0 g of the Hydrogel Composition is administered per teat of the animal.

Embodiment 73

The method of Embodiment 72, wherein about 1.0 to about 4.0 g of the Hydrogel Composition is administered per teat of the animal.

Embodiment 74

The method of Embodiment 71, wherein the milk product is milk, yogurt or cheese.

Embodiment 75

The method of Embodiment 74, wherein the milk is dry or fluid milk.

Embodiment 76

The method of Embodiment 71, wherein the animal is a livestock animal.

Embodiment 77

The method of Embodiment 76, wherein the livestock animal is a heifer or cow.

Embodiment 78

The method of Embodiment 71, wherein the Hydrogel Composition is administered via intramammary infusion or by dipping the teat.

Embodiment 79

The method of Embodiment 71, wherein the animal is a heifer or cow and wherein the administration is achieved by intramammary infusion during the transition period or the dry period.

Embodiment 80

The method of Embodiment 71, wherein the Hydrogel Composition is administered during the postpartum period of a non-lactating animal.

Embodiment 81

The method of Embodiment 71, wherein the Hydrogel Composition is administered during the prepartum period of an animal.

Embodiment 82

The method of Embodiment 71, wherein the Hydrogel Composition is administered prior to infection of a healthy animal.

Embodiment 83

The method of Embodiment 71, wherein the composition is Formulation A4, I or I4 as disclosed herein.

Embodiment 84

A method for reducing the withholding time of milk obtained from an animal being treated for mastitis for the production of a milk product, wherein the Hydrogel Composition is administered to the animal.

Embodiment 85

The method of Embodiment 84, wherein about 0.5 to about 5.0 g of the Hydrogel Composition is administered per teat of the animal.

Embodiment 86

The method of Embodiment 85, wherein about 1.0 to about 4.0 g of the Hydrogel Composition is administered per teat of the animal.

Embodiment 87

The method of Embodiment 84, wherein the milk product is milk, yogurt or cheese.

Embodiment 88

The method of Embodiment 87, wherein the milk is dry or fluid milk.

Embodiment 89

The method of Embodiment 84, wherein the animal is a livestock animal.

Embodiment 90

The method of Embodiment 89, wherein the livestock animal is a heifer or cow.

Embodiment 91

The method of Embodiment 84, wherein the Hydrogel Composition is administered via intramammary infusion or by dipping the teat.

Embodiment 92

The method of Embodiment 84, wherein the animal is a heifer or cow and wherein the administration is achieved by intramammary infusion during the transition period or the dry period.

Embodiment 93

The method of Embodiment 84, wherein the Hydrogel Composition is administered during the postpartum period of a non-lactating animal.

Embodiment 94

The method of Embodiment 84, wherein the Hydrogel Composition is administered during the prepartum period of an animal.

Embodiment 95

The method of Embodiment 84, wherein an antimicrobial agent is also administered to the animal.

Embodiment 96

The method of Embodiment 95, wherein the antimicrobial agent is ceftiofur hydrochloride.

Embodiment 97

The method of Embodiment 84, wherein the composition is Formulation A4, I or I4 as disclosed herein.

Embodiment 98

A method for reducing the withholding time of milk obtained from an animal being prophylactically treated for mastitis for the production of a milk product, wherein a Hydrogel Composition is administered to the animal.

Embodiment 99

The method of Embodiment 98, wherein about 0.5 to about 5.0 g of the Hydrogel Composition is administered per teat of the animal.

Embodiment 100

The method of Embodiment 99, wherein about 1.0 to about 4.0 g of the Hydrogel Composition is administered per teat of the animal.

Embodiment 101

The method of Embodiment 98, wherein the milk product is milk, yogurt or cheese.

Embodiment 102

The method of Embodiment 101, wherein the milk is dry or fluid milk.

Embodiment 103

The method of Embodiment 98, wherein the animal is a livestock animal.

Embodiment 104

The method of Embodiment 103, wherein the livestock animal is a heifer or cow.

Embodiment 105

The method of Embodiment 98, wherein the Hydrogel Composition is administered via intramammary infusion or by dipping the teat.

Embodiment 106

The method of Embodiment 98, wherein the animal is a heifer or cow and wherein the administration is achieved by intramammary infusion during the transition period or the dry period.

Embodiment 107

The method of Embodiment 98, wherein the Hydrogel Composition is administered during the postpartum period of a non-lactating animal.

Embodiment 108

The method of Embodiment 98, wherein the Hydrogel Composition is administered during the prepartum period of an animal.

Embodiment 109

The method of Embodiment 98, wherein the composition is Formulation A4, I or I4 as disclosed herein.

Embodiment 110

A method of using a Hydrogel Composition as a teat sealant in an animal in need thereof.

Embodiment 111

The method of Embodiment 110, wherein about 0.5 to about 5.0 g of the Hydrogel Composition is used per teat of the animal.

Embodiment 112

The method of Embodiment 111, wherein about 1.0 to about 4.0 g of the Hydrogel Composition is used per teat of the animal.

Embodiment 113

The method of Embodiment 110, wherein the animal is a livestock animal.

Embodiment 114

The method of Embodiment 113, wherein the livestock animal is a heifer or cow.

Embodiment 115

The method of Embodiment 110, wherein the Hydrogel Composition is used during the transition period through the dry period of the heifer or cow.

Embodiment 116

The method of Embodiment 110, wherein the Hydrogel Composition is a polymerizing hydrogel.

Embodiment 117

The method of Embodiment 110, wherein an antimicrobial agent is also used for the animal.

Embodiment 118

The method of Embodiment 117, wherein the antimicrobial agent is ceftiofur hydrochloride.

Embodiment 119

The method of Embodiment 110, wherein the composition is used by infusion into the teat of the animal.

Embodiment 120

The method of Embodiment 110, where the composition is used by external application to the teat of the animal.

Embodiment 121

The method of Embodiment 110, wherein the composition is Formulation A4, I or I4 as disclosed herein.

Embodiment 122

Use of a Hydrogel Composition in the manufacture of a medicament for the treatment of a microbial infection in an animal.

Embodiment 123

The use of Embodiment 122, wherein the microbial infection is mastitis.

Embodiment 124

The use of Embodiment 122, wherein the medicament is for teat dipping.

Embodiment 125

The use of Embodiment 122, wherein the medicament is for intramammary infusion.

Embodiment 126

The use of Embodiment 122, wherein the animal is a livestock animal.

Embodiment 127

The use of Embodiment 126, wherein the livestock animal is a heifer or cow.

Embodiment 128

The use of Embodiment 122, wherein the composition is Formulation A4, I or I4 as disclosed herein.

Embodiment 129

Use of a Hydrogel Composition in the manufacture of a medicament for preventing or treating mastitis in an animal.

Embodiment 130

The use of Embodiment 129, wherein the medicament is for teat dipping.

Embodiment 131

The use of Embodiment 129, wherein the medicament is for intramammary infusion.

Embodiment 132

The use of Embodiment 129, wherein the animal is a livestock animal.

Embodiment 133

The use of Embodiment 132, wherein the livestock animal is a heifer or cow.

Embodiment 134

The use of Embodiment 129, wherein the composition is Formulation A4, I or I4 as disclosed herein.

Further to the foregoing, the present disclosure particularly can relate to a method of treating an animal, the method comprising administering a hydrogel composition to mammary tissue of the animal. In one or more embodiments, the method can be further defined in relation to one or more of the following statements, which can be combined in any number and order.

The hydrogel composition can be administered one or both of externally and internally to the mammary tissue.

The hydrogel composition can be administered to a teat of the animal or to a plurality of teats of the animal.

The hydrogel composition can be administered to an external surface of the teat or teats.

The hydrogel composition can be infused into the teat or teats.

The hydrogel composition can be administered to the animal in an amount of about 0.5 g to about 5.0 g per teat.

The animal can be a livestock animal.

The animal can be a heifer or cow.

The hydrogel composition can be administered during a transition period that extends through a dry period of the heifer or cow.

The hydrogel composition can be a polymerizing hydrogel.

The hydrogel composition can comprise a water soluble polyvinyl alcohol macromer.

The hydrogel composition can comprise a polyol.

The hydrogel composition can have an adhesion peel test pull force value of about 0.05N to about 0.5N.

The hydrogel composition can be configured such that a fully dehydrated sample of the hydrogel composition has a swelling range of about 100% to about 1000% of starting weight of the fully dehydrate sample when combined with a PBS solution at a temperature of about 25° C. and a relative humidity of about 60%.

The hydrogel composition can be Formulation A4, Formulation I, or Formulation I4.

The method further can comprise administering an antimicrobial agent to the mammary tissue of the animal. In particular, the antimicrobial agent can be ceftiofur hydrochloride.

The administering can be effective for treating or preventing a microbial infection in the mammary tissue of the animal. In particular, the microbial infection can be mastitis.

Treating or preventing the microbial infection can comprise treating or preventing a bacterial invasion of the mammary tissue.

The method can comprise forming a physical barrier in a teat canal of the animal, said physical barrier being effective for prophylactic treatment of mammary disorders.

The treatment can be effective such that milk obtained from the animal during said treatment is suitable for use in the production of a milk product. In particular, the milk product can be one or more of dry milk, liquid milk, yogurt, and cheese.

The hydrogel composition can be administered during a postpartum period of a non-lactating animal.

The hydrogel composition can be administered during a pre-partum period of the animal.

The hydrogel composition can be administered to a healthy animal exhibiting no symptoms of an infection of the mammary tissue.

The treatment can be effective to reduce the period of time during which milk obtained from the animal must be withheld from use in the production of a milk product.

The treatment can be effective to reduce the period of time during which milk obtained from an animal being prophylactically treated for mastitis must be withheld from use in the production of a milk product.

The hydrogel composition can be adapted to act as a teat sealant in the treated animal.

Still further to the foregoing, the present disclosure particularly can relate to a system for forming a physical barrier in a teat of an animal. In exemplary embodiments, the system can comprise: a hydrogel composition comprising a water soluble polyvinyl alcohol macromer and a polyol; and an injection device adapted for infusing the hydrogel composition into a teat cistern of the teat of the animal. In some embodiments, the system further can comprise an antimicrobial agent. Two or more components of the hydrogel composition can be stored in separate containers of the injection device (e.g., separate barrels of a multi-barrel syringe). Alternatively, separate components of the hydrogel composition may be stored in containers, and the desired amounts of the components may be added to the injection device prior to administration of the hydrogel composition. The delivery device can include a variety of elements including, but not limited to, syringes, tubing, needles, spray adapters, mixers, and the like.

BRIEF DESCRIPTION OF THE DRAWINGS

Figure 1:
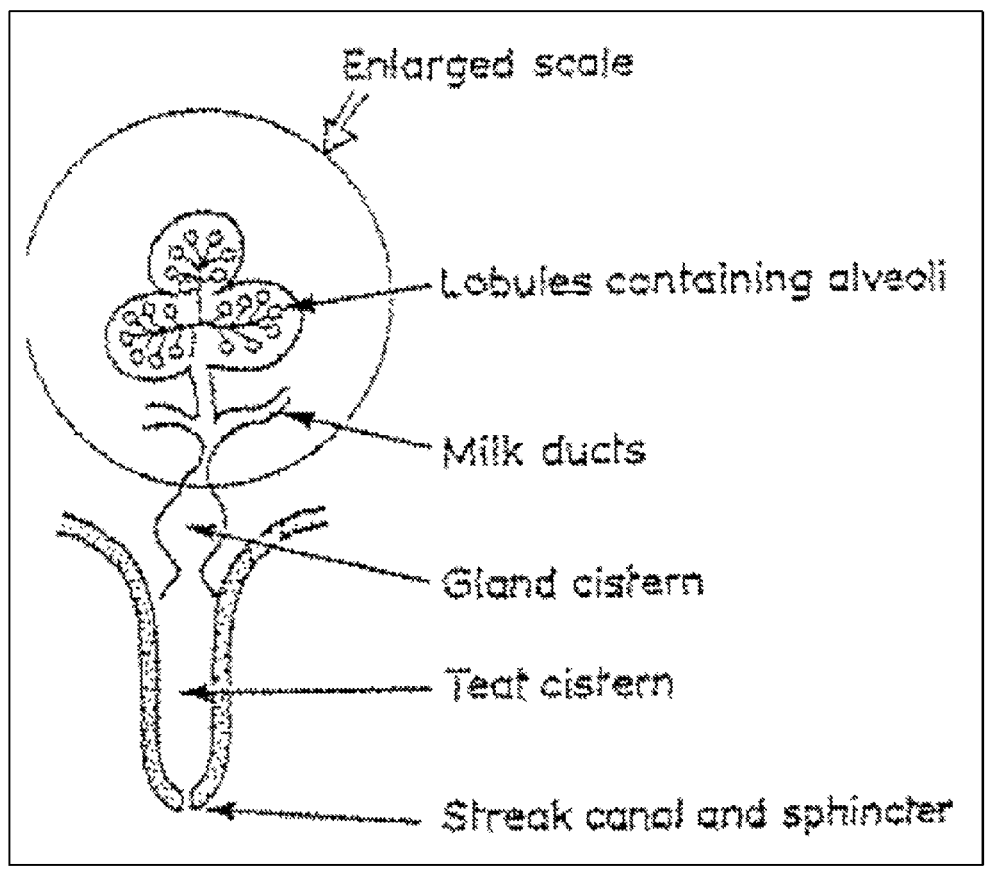
Figure 2:
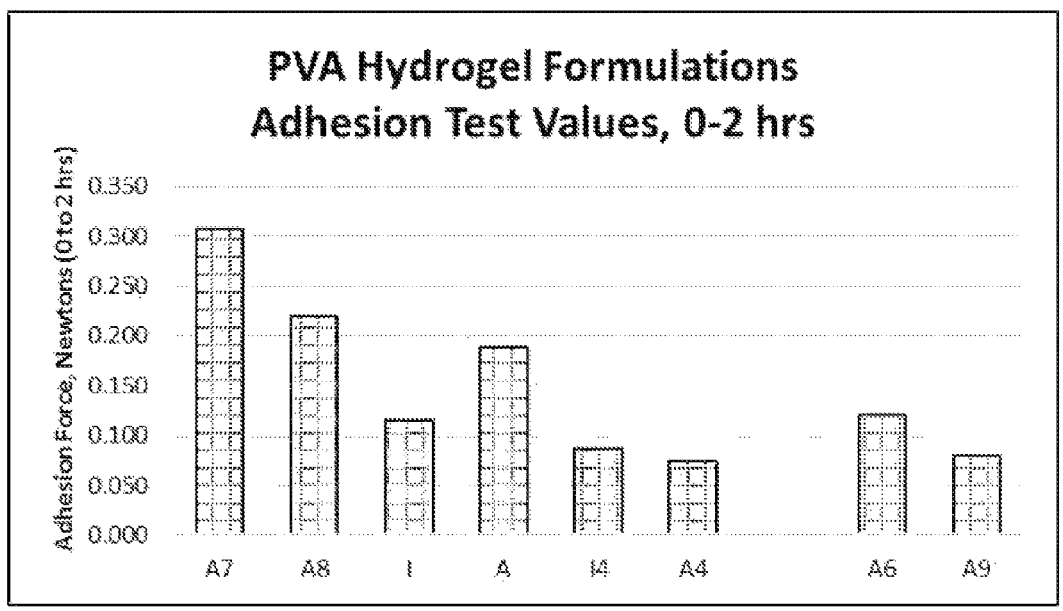
Figure 3:
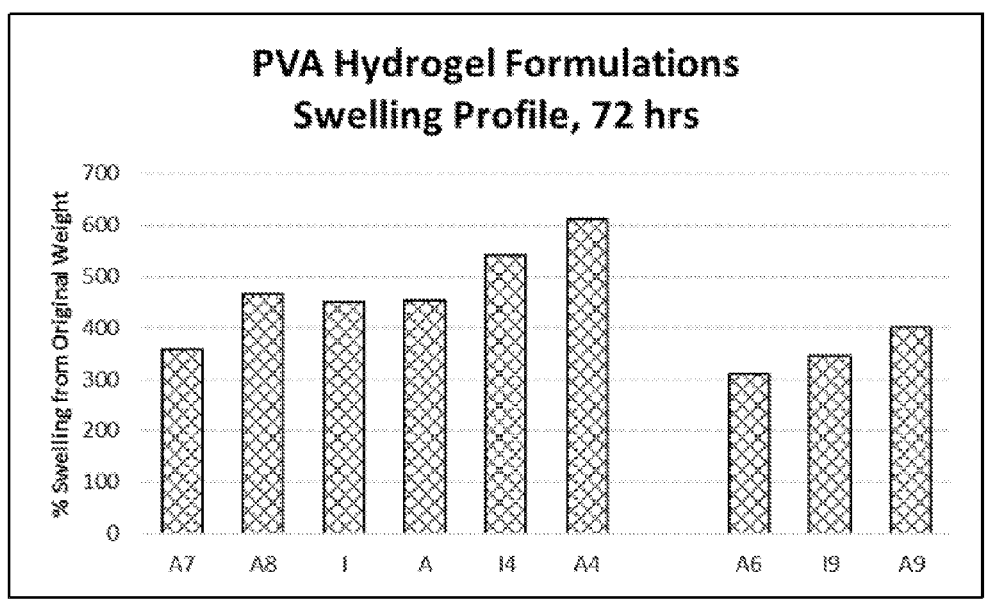

Having thus described the disclosure in the foregoing terms, reference will now be made to the accompanying drawings, which are not necessarily drawn to scale, and wherein:

FIG. 1 is a schematic of an animal teat;

FIG. 2 is a chart of adhesion testing results for various formulations according to embodiments of the present disclosure; and FIG. 3 illustrates percent swelling of various formulations according to embodiments of the present disclosure.

DETAILED DESCRIPTION OF THE PREFERRED EMBODIMENTS

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

Compositions useful for forming hydrogel teat sealants, among other applications, are disclosed. The compositions include a macromolecular monomer (termed herein a "macromer") that forms a hydrogel. The hydrogel is preferably formed in situ on or in the teat using a free radical initiation system or redox reaction.

In a preferred embodiment, the hydrogel is formed from macromers that are polymerized using a redox system. The reducing component includes the macromer and a reducing agent, with optionally a stabilizer and other additives. The oxidizing component includes the macromer and an oxidizing agent, with optionally a stabilizer and other additives. Both components are solutions.

The two component formulation is applied to the teat by a spray or stream from a syringe, pump, spray nozzle, aerosol, dip, or other type of device. The two components are desirably mixed through a static mixer and delivered to the teat. A combination of the spray and stream may be applied in a method similar to a shower head, whereby multiple streams provide the simulated broad coverage of a spray application. The macromers and other additives are sprayed or streamed to the teat whereupon they crosslink in situ to form the hydrogel-based teat sealant. For application inside the teat, as in the teat cistern, a syringe may be used.

The composition may further include one or more pharmaceutical agents, such as antimicrobial agents. The pharmaceutical agent or agents will become trapped in the hydrogel upon its formation and will be released from the hydrogel immediately or over a period of time.

In one embodiment the invention is a method and composition for forming a hydrogel physical barrier on a tissue surface, preferably on the surface of an animal teat.

In another embodiment the invention is a method and composition for forming a hydrogel physical barrier in a tissue, preferably in the teat cistern or streak canal of an animal.

Definitions

The term "mammary tissue" as used herein refers to any tissue related to the milk-producing glands of a mammal. Mammary tissue specifically can include a teat and its associated elements. Mammary tissue can be internal tissue, such as tissue related to the teat canal (inclusive of the open canal itself), tissue related to the teat cistern (inclusive of the open cistern itself), tissue related to the gland cistern (inclusive of the cistern itself), milk ducts, lobules containing alveoli, fatty tissue proximate the mammary tissue, and epidermal tissue surrounding the mammary tissue. Mammary thus further includes the external surfaces of the mammary tissue, such as the outer surface of the teat and the immediately surrounding epidermal tissue. See, for example, the illustration of the elements of an animal teat shown in FIG. 1, all of said elements being exemplary of mammary tissue encompassed by the present disclosure.

The term "teat sealant" as used herein refers to compositions and devices used to form a physical barrier on the surface of or inside an animal teat. A teat sealant can be on the teat surface, inside the teat streak canal, and/or inside the teat cistern.

The term "hydrogel" as used herein refers to a material having an aqueous phase with an interlaced polymeric component, with at least 10% and up to 95% of its weight as water.

The term "antimicrobial" as used herein refers to a substance that kills or inhibits the growth or reproduction of microorganisms such as bacteria, fungi, yeast, or protozoans. Examples are provided below.

The term "solution" as used herein refers to solutions, suspensions, or dispersions, unless otherwise stated.

The term "spray" as used herein refers to an atomized composition, such as comprised of small or large liquid droplets, such as applied through an aerosol applicator or pump spray applicator for the intended purpose of delivering a broad application of the composition.

The term "stream" as used herein refers to a continuous, direct, and focused application of the composition.

The term "infusion" as used herein refers to the continuous introduction of a fluid or solution into a cavity, vein or cistern.

The term "animal" as used herein refers to any female mammal which has a lactation period. The term "animal" preferably includes livestock animals, such as cows.

The term "heifer" as used herein refers to any young female cow that has not given birth to a calf.

The term "dry period" as used herein refers to the non-lactating phase of the lactation cycle of a cow. It occurs between the end of one lactation and the beginning of the next lactation.

The term "transition period" as used herein refers to the period before and after calving that includes the physiological, metabolic and endocrine changes associated with cessation of milk production for the non-lactating period (dry period) of the lactation cycle in a cow, including also the changes associated with the preparation for calving, preparation for milk production for the calf, calving and the period immediately following calving.

The term "milk product" as used herein refers to a product containing any amount of milk in liquid or powder form. It also includes cheese and yogurt.

The term "postpartum" as used herein refers to the period of time beginning immediately after calving and extending for about six weeks.

The term "prepartum" as used herein refers to the period of time during pregnancy, which is prior to calving.

The term "periparturient" as used herein refers to the period immediately before and after calving.

The term "involution" as used herein refers to the first two to three weeks after cessation of milk production in a cow.

The term "keratin plug" as used herein refers to keratin-based occlusion of the teat canal/streak canal of a cow following cessation of milk production for the dry period.

The term "bacterial invasion" as used herein refers to movement of pathogenic microorganisms that proliferate into bodily tissue or bodily cavities, resulting in tissue injury that can progress to disease.

The term "Hydrogel Composition" as used herein refers to a hydrogel composition formed from the following: a PVA macromer in an amount between about 2 and 10 wt %; and glycerol in an amount between about 5 and 20 wt %; and wherein the hydrogel has an Adhesion Test value of between about 0.05 to 0.5N and a swelling range of between about 100% to 1000% of original weight.

In some embodiments, this composition is a hydrogel composition wherein the glycerol is present in an amount of about 10 to about 16 wt %.

In some embodiments, this composition does not include a filler, and the 2-hour adhesion value is about 0.05N to about 0.2N.

In some embodiments, this composition has an Adhesion Test value which is about 0.05N to about 0.35N.

In another embodiment, this composition is a hydrogel composition which further includes a filler and wherein the Adhesion Test value is about 0.05N to about 0.2N.

More particularly, this composition has an Adhesion Test value which is about 0.07N to about 0.35N.

More particularly, this composition has the PVA macromer present in an amount between about 6-9 wt %. In another embodiment, this composition further includes an active pharmaceutical agent, such as an antimicrobial agent.

Formulation Characteristics

This patent covers formulations that have a unique combination of deliverability, swelling, and adhesion. More specifically, these formulations have a PVA concentration by weight of about 2% to about 10% by weight (preferred range of about 4.5% to about 9% by weight) and a glycerol concentration range of about 5% to about 16% by weight (preferred range of about 10% to about 16% by weight). For teat sealants the range of glycerol content is about 5% to about 20% by weight, preferably about 10% to about 16% by weight. Characteristics of the hydrogel are a swelling range of about 100% to about 1000% of original weight (preferred range of about 400% to about 650%), and an Adhesion Test value of about 0.05 to about 0.5N, about 0.05N to about 0.35N, or about 0.07N to about 0.35N.

Components of the Composition

The composition includes a PVA macromer that can quickly crosslink after delivery, to form a teat sealant in or on a teat. The composition further includes aqueous media, redox components, stabilizers for the redox components, thickening agents, and optionally one or more antimicrobial agents, and may include additives such as an absorbent, and other active agents.

PVA Macromer:

The macromer can be made by general synthetic methods known to those skilled in the art. The preferred macromers can be made as described in U.S. Pat. Nos. 5,508,317, 5,583,163, 5,583,163, 5,665,840, 5,807,927, 5,849,841, 5,932,674, 5,939,489, and 6,011,077. The macromer has at least two pendant chains containing groups that can be crosslinked. The term "group" includes single polymerizable moieties containing vinyl groups such as an acrylate and acrylamide. The crosslinkers are desirably present in an amount of from about 0.01 to 10 about millimole of crosslinker per gram of backbone (mmol/g), more desirably about 0.05 to about 1.0 mmol/g. The macromer can contain more than one type of crosslinkable group. The pendant chains are attached via the hydroxyl groups of the backbone. Desirably, the pendant chains having crosslinkable groups are attached via cyclic acetal linkages to the 1,2-diol or 1,3-diol hydroxyl groups. Desirable crosslinkable groups include (meth)acrylamide, (meth)acrylate, styryl, vinyl ester, vinyl ketone, and vinyl ethers. Particularly desirable are ethylenically unsaturated functional groups.

A particularly desirable crosslinker is N-acryloyl-aminoacetaldehyde dimethylacetal (NAAADA) (CAS 49707-23-5) in an amount from about 1 to 500 crosslinkers per macromer. A particularly preferred macromer has a PVA backbone (67 kDa, 12% acetate incorporation) modified with 0.1 mmol/g N-acrylamidoacetaldehyde dimethyl acetal (NAAADA) pendant polymerizable groups (PVA 888-7X) (Moxiol 8-88 (88% hydrolyzed) with 7 crosslinks per chain). Hydrophilicity of the PVA macromer can be adjusted by reacting with hydrophobic acetal or hydrophilic ammonium acetal. Macromers can also be modified to enhance the hydrogel tackiness, change the solution viscosity and gelation speed, and to change the hydrogel water content, absorption capability, and mechanical properties.

Crosslinking Initiators:

The macromers are polymerized by redox free radical polymerization using a two-part redox system. One part of the system contains a reducing agent such as ferrous salt. Various ferrous salts can be used, such as ferrous gluconate dihydrate, ferrous sulfate, ammonium ferrous sulfate, ferrous lactate dihydrate, or ferrous acetate. The amount of reducing agent used will vary. In one embodiment, the percent range for ferrous salt in the reductant component is about 0.06 to about 0.18% by weight of the reductant component. The other part of the composition contains an oxidizing agent such as hydrogen peroxide. The amount of oxidizing agent used will also vary. In one embodiment, the amount of oxidizing agent in the oxidant component is about 0.05 to about 0.12 grams in 10 mL. Either or both of the redox solutions can contain macromer. The agents react to initiate the polymerization of the macromer to generate a crosslinked hydrogel. Other reducing agents can be used, including but not limited to, iron, titanium trichloride, cysteine, and sodium thiosulfate. Other oxidizing agents that can be used include, but are not limited to, ammonium persulfate, ceric (IV) salt, and t-butyl hydroperoxide.

Stabilizers:

The oxidizing component is stabilized by peroxide stabilizers such as sodium pyrophosphate or organophosphonates (Dequest® 2010 and Dequest® 2060S, Solutia Inc.). Phosphonates are chelants that offer stabilization of peroxide systems. Dequest® 2010 is 1-hydroxy ethylene-1,1-diphosphonic acid. The active in Dequest 2060S is diethylenetriamine penta(methylene phosphonic acid). Other chelating agents are EDTA and citric acid. These can be added in amounts as recommended by the manufacturer, generally less than 200 ppm. The reducing component is stabilized using antioxidant stabilizers, including but not limited to ascorbic acid (vitamin C), glutathione, lipoic acid, uric acid, carotenes (vitamin A), BHT, BHA, propyl gallate, and α-tocopherol (vitamin E). Generally the antioxidant stabilizer is added at below 1% by weight. Antioxidants also function to stabilize the macromers by inhibiting polymerization.

Antimicrobial Active Agents:

There are a variety of antibacterial agents available for use in animals. These antibacterial agents include, but are not limited to, the following: macrolides, for example, tulathromycin (Draxxin®), tildipirosin (Zuprevo®), tilmicosin (Micotil®), tylosin phosphate (Tylan®), and gamithromycin (Zactran®); cephalosporins, for example, ceftiofur sodium (e.g., Naxcel® and Excenel®), ceftiofur hydrochloride (e.g., Excenel RTU®, Excenel RTU EZ®, Spectramast®), ceftiofur crystalline free acid (Excede®), cefovecin sodium (Convenia®), and cefpodoxime proxetil (Simplicef®); lincosaminide antibiotics, for example, lincomycin (Lincomix®), pirlimycin hydrochloride (Pirsue), and clindamycin hydrochloride (Antirobe®); fluoroquinolones, for example, danofloxacin (Advocin®), enrofloxacin (Baytril®), and marbofloxacin (Zeniquin®); and tetracyclines, for example, chlortetracycline, oxytetracycline, and doxycycline. Other antibacterial agents include, but are not limited to, amoxicillin trihydrate and clavulonic acid (Clavamox®), spectinomycin (Adspec®), potentiated sulfonamides including trimethoprim/sulfadiazine (Tucoprim®) and sulfadimethoxine/ormetoprim (Primor®); and florfenicol (for example, Nuflor® and Nuflor® Gold). An antimicrobial agent may be administered simultaneously or sequentially with the compositions of the present invention.

Density Modifiers/Thickening Agents:

Agents may be added to provide weight to the hydrogel and prevent the hydrogel from migrating up the teat cistern and into the gland cistern during the dry period. Examples of appropriate density modifiers or thickening agents include but are not limited to the following: polyvinyl alcohol, dextrin, distarch phosphate, edible gelatin, polydextroses, propylene glycol, methyl cellulose, oxidized starch, ammonium dihydrogen phosphate, Glucoamylase, Calcium dihydrogen phosphate, Calcium malate (DL1), Calcium monohydrogen phosphate, Carotene, L-glutamic acid, Magnesium hydrogen phosphate, Maltitol, Mannitol, Disodium dihydrogen phosphate, Starch acetate, Polydextroses, Processed Eucheuma seaweed, Propylene glycol, Gellan gum, Edible gelatin, Carrageenan, Sorbitol, Methyl cellulose, Disodium ethylenediamenetetraacetate, Calcium disodium ethylenediamenetetraacetate, Potassium dihydrogen citrate, Potassium dihydrogen phosphate, Oxystearin, Hydroxypropyl distarch phosphate, Hydroxypropyl methyl cellulose, Tara Gum, Tragacanth Gum, Xanthan Gum, Guar Gum, Gum Arabic and Potassium alginate.

The thickener can be added at about 2% to about 10% by weight of the composition. The final density of the formulation may be about 1.1 to 2.0 g/cc.

Other Components:

The composition may additionally contain one or more additives such as stabilizers, defoamers, pore forming agents, plasticizers, penetration enhancers, colorants, wettings agents, leveling agents, thickeners, fillers, opacifying agents, and absorbents.

Other additives can include pain relief agents, analgesics, and/or anti-inflammatories such as, but not limited to: lidocaine, ibuprofen, diclofenac, and capsaicin. The composition may contain various additives including but not limited to glycerol, polyethylene glycol, polypropyl glycol, polybutylene glycol, polyacrylic acid, celluloses, calcium alginate, sucrose, lactose, fructose, sorbitol, mannitol, zylitol, dextrans, hyaluronic acid, polyacrylamidopropyltrimethyl ammonium chloride, calcium chloride, APOSS (Octaammonium-POSS (polyhedral oligomeric silsesquioxane)), and poly(2-acrylamido-2-methylpropane sulfonic acid). These can be added to the composition to improve the performance of the teat sealant including adhesion, tackiness, and to change the water content, water uptake, and moisture vapor transmission (MVTR).

The composition is steam sterilizable and can be stored or packaged under vacuum or an inert atmosphere of nitrogen or argon in order to prevent oxidation of the reductant initiator component.

Adhesion Control:

The above described beneficial characteristics for a teat sealant such as adhesion, swelling, tack, moisture handling, fluid absorption, and viscosity can be achieved with certain formulations. In particular, it has been found that 5 to 16% by weight glycerol or like polyol provides the desired degree of adhesion and other qualities for a hydrogel teat sealant formed from PVA based macromers.

Exemplary Uses for the Hydrogel Compositions

Hydrogel compositions as described herein can exhibit characteristics making them beneficial for a variety of uses. As further described below, the compositions can be beneficial in methods of treating or preventing multiple conditions in relation to mammary tissue of mammals, particularly non-human animals (although treatments of humans is not necessarily excluded according to some embodiments of the disclosure). In one or more embodiments, the compositions are particularly useful as teat sealants in light of their ability to gel in situ and provide adhesive properties. The desired characteristics of the presently disclosed compositions can vary depending upon the specific usage of the compositions, such as where the composition will be administered, how it will be administered, and other factors. In some embodiments, however, the hydrogel compositions suitable for use as teat sealants can exhibit specific characteristics as further described below. In one or more embodiments, characteristics causing the compositions to be useful as teat sealants may also extend to the further uses of the composition, as otherwise described herein.

The hydrogel compositions specifically can be configured so as to be easily removed from a teat (or other tissue) to which it has previously been applied. Where the sealant is placed intra-teat (e.g., in a canal and/or cistern), it is desirably removed by stripping, most desirably in the first strip. In addition, the sealant can be configured so as to be removable as a single piece, or as multiple large pieces.

The hydrogel composition can be configured for administration in a substantially non-polymerized or non-crosslinked form so that polymerization and/or crosslinking may take place in situ. The as-formed composition thus can be configured to be conformable and compliant so that it conforms to the topography of the mammary tissue and/or canal or cistern to which it is administered and is non-irritating to the animal. Conformability will also extend the longevity of the administered composition. The presently disclosed composition is also preferably strong enough that it can be peeled off the mammary tissue and can be removed in one cohesive unit leaving little material behind. Thus, it is often desirable to control the adhesion of the composition. This can be achieved by modifying the macromer with hydrophilic or hydrophobic side chains, including an additional monomer, or adding specific additives such as surfactants, organic solvents, or amphiphilic block copolymers (e.g. pluronics).

Hydrogels that have a specific combination of adhesion and swelling will exhibit properties that are particularly useful in the creation of removable barriers compatible with human or animal tissue. These hydrogels can be used as plugs at the macro or micro level, and the appropriate range of adhesion will allow these in situ formed hydrogel to adhere to tissue and stay in place all while being easily removed manually. In addition, if these hydrogels are plugged in a location where a barrier to retain/absorb fluid is necessary, the hydrogel can naturally absorb the fluid while remaining in their desired location.

The hydrogel teat sealant compositions of the present disclosure are beneficially safe and stable. As such, the composition ingredients specifically can be biocompatible or non-irritating in the amounts present in the final hydrogel teat sealant. The composition preferably is prepared so as to be sterile and able to preserve the activity of any optionally included drug.

The viscosity of the composition is preferably within a range so as to be suitable for the delivery method. The viscosity can be controlled so that the composition can be sprayed or streamed onto or into the mammary tissue in a manner such that the composition may gel rapidly, substantially conform to the surrounding tissue, provide a stable coating, filler, and/or sealant, and yet be easily removable. Viscosity can be controlled by selection of the molecular weight of the macromer and adjustment of the relative concentrations of the macromer and the further components of the hydrogel compositions.

Upon combination of the components of the hydrogel composition, the composition can exhibit a structural change such that gelation of the macromer composition occurs. Gelation can result from crosslinking of the polymeric material. Gelation preferably is sufficiently rapid to avoid material loss during application, e.g., to avoid run off of the composition from the place of application. The gelling time can be about 5 minutes or less, preferably less than about three minutes, more preferably less than about 0.5 minute, and, in some situations, as low as about 10 seconds or less. The gelling time can be controlled by many factors, such as adjusting the concentration of initiators, varying the type of initiator used, altering the crosslinking group of the PVA macromer, adjusting the solids content of the composition, and/or altering the mixing mechanism that is used.

In one or more embodiments, the present disclosure particularly can relate to one or more methods for treating a subject. More particularly, the disclosure can relate to any of the following: a method for treating an animal; a method for treating a mammal; a method for treating a female mammal; a method for treating a human mammal; a method for treating a non-human mammal; a method for treating a livestock animal; a method for treating a cow; a method for treating a heifer. The present methods of treatment particularly can relate to administering a hydrogel composition as described herein to mammary tissue of the subject being treated. The hydrogel composition may be administered as separate components that are configured to mix and/or gel after administration. The hydrogel composition may be administered as a pre-mixed combination of the separate components but in a substantially non-gelled state. The hydrogel composition may be administered in a partially gelled state.

The hydrogel composition may be administered in a variety of manners. In some embodiments, the hydrogel composition can be administered externally (e.g., to an outer surface of mammary tissue, such as a teat). In some embodiments, the hydrogel composition can be administered internally (e.g., by injecting into the mammary tissue or passage into a canal and/or cistern surrounded by mammary tissue). In particular embodiments, the hydrogel composition can be administered to a teat or to a plurality of teats of a subject. More particularly, the hydrogel composition can be administered to an external surface of the teat or teats, such as by spraying, dipping, brushing, or otherwise contacting the external surface of the teat with a liquid form of the hydrogel composition. In further embodiments, the hydrogel composition can be infused into the teat or teats, such as by passage of the liquid composition directly into a canal and/or cistern of the teat or teats.

In one or more embodiments, the presently disclosed hydrogel compositions can be used for treating or preventing a microbial infection in the mammary tissue. In particular, administration of the hydrogel composition can be effective for treating or preventing a bacterial invasion of the mammary tissue, which bacterial invasion may otherwise cause an infection. In specific embodiments, the present methods may be effective for treating or preventing mastitis.

In some embodiments, the present methods particularly can relate to forming a physical barrier in a teat canal and/or a teat cistern. Preferably, such physical barrier can be effective for prophylactic treatment of one or more mammary disorders. For example, the presence of the physical barrier can be effective to treat or prevent mastitis.

In further embodiments, administration of a hydrogel composition as described herein can be effective for improving milk production and expanding the usefulness of milk obtained from an animal being treated as described herein. For example, when the present hydrogel composition is utilized as described herein (e.g., as a teat sealant or as otherwise administered internally and/or externally to a teat or teats), milk that is obtained from the animal during the time of treatment may be used immediately in the production of one or more milk products. Further, while it is typical procedure for produced milk to be withheld from use in production of milk products when the producing animal is suffering from a condition, such as mastitis, and/or is being treated for a condition, such as mastitis, use of a hydrogel composition as described herein can minimize and/or eliminate such withholding period. As such, in the treatment of an animal as described herein using the disclosed hydrogel compositions, the period of time during which milk obtained from the animal must be withheld from use in the production of a milk product can be significantly reduced. Likewise, when an animal is being treated prophylactically for a condition, such as mastitis, by administration of a hydrogel composition as described herein, the period of time during which the produced milk must be withheld from use in the production of a milk product can also be reduced. In one or both cases, the time for which the produced milk must be withheld from use in production of a milk product can be reduced by at least 10%, by at least 25%, by at least 50%, or by at least 75%. As discussed above, it is understood that a milk product can relate to any consumer product that includes milk as the sole ingredient thereof, as a major ingredient thereof, or as a substantial ingredient thereof.

Non-limiting examples of such milk products include dry milk, liquid milk, yogurt, and cheese.

The hydrogel composition may be administered a single time and be allowed to remain in place for a defined period—such as about 1 day, about 2 days, about 3 days, about 4 days, about 5 days, about 6 days, about 1 week, about 2 weeks, about 3 weeks, about one month, about two months, about three months, or even longer. In some embodiments, the hydrogel composition may be administered, left in place for a time, removed for a time, and then administered again. Any number of cycles of administration and removal may be used. In some embodiments, it can be desirable for the hydrogel composition to be effective such that only a single administration is needed for the defined treatment period. The time of administration of the hydrogel composition to an animal, such as a female animal (e.g., a cow, more particularly a heifer), may relate to a reproduction cycle of the animal. For example, in some embodiments, the hydrogel composition can be administered during a postpartum period of an animal, more particularly of a non-lactating animal. In another exemplary embodiment, the hydrogel composition can be administered during a prepartum period of an animal. In further embodiments, the hydrogel composition can be administered during a transition period of a cow. More specifically, the transition period can extend through a dry period of the cow. The periods of administration exemplified above can specifically indicate that the hydrogel composition is applied a single time and remains in place for the duration of the noted period. In some embodiments, the hydrogel composition may be administered during the noted period and remain in place for only a portion of the noted period. In other embodiments, the hydrogel composition may be administered during the noted period, and the composition may be removed and replaced one or more times during the noted period.

The present methods may be applied to subjects in a variety of conditional states. For example, the hydrogel composition may be administered to a subject that actively exhibits symptoms of an infection of the mammary tissue. In some embodiments, the hydrogel composition can be administered to a healthy subject exhibiting no symptoms of an infection of the mammary tissue. Further, the hydrogel composition can be administered to a subject that is believed to be at risk for an infection of the mammary tissue. In one or more embodiments, the hydrogel composition can be adapted to act as a teat sealant in the treated animal.

The hydrogel composition can be particularly beneficial for use as discussed above in light of the various characteristics of the compositions. For example, the nature of the hydrogel composition as being a polymerizing hydrogel can be beneficial in that the hydrogel composition can be administered in a liquid (e.g., flowable) form and then allowed to "polymerize" (e.g., via crosslinking) to become solid or semi-solid and thus be substantially or completely non-flowable.

The amount of the hydrogel composition administered to the subject can vary. In some embodiments, the amount of the hydrogel composition that is administered can be relative to the administration site. For example, the hydrogel composition can be administered in an amount of at least 0.1 g per site, at least 0.25 g per site, at least 0.5 g per site, or at least 1 g per site. In some embodiments, the hydrogel composition can be administered in an amount of about 0.1 g to about 10 g per site, about 0.25 g to about 7.5 g per site, about 0.5 g to about 5.0 g per site, about 0.75 g to about 4.5 g per site, or about 1 g to about 4 g per site. As non-limiting examples, a single site of administration may be a single teat, a single site of administration may be the outer surface of a single teat, a single site of administration may be a single teat canal, or a single site of administration may be a single teat cistern.

The hydrogel composition utilized in the presently described methods can comprise a combination of any of the materials otherwise described herein. In particular, the hydrogel composition can comprise at least one PVA macromer. In some embodiments, the hydrogel composition comprises at least one polyol, such as glycerol.

In one or more embodiments, the hydrogel composition may be described in relation to its post-administration form. In such form, the composition preferably includes the PVA macromer and at least one polyol. The composition likewise may include at least some amount of one or more crosslinking initiators and/or one or more by-products or remnants of the crosslinking initiators. In some embodiments, the composition may include at least some amount of one or more stabilizer. In some embodiments, the composition may include one or more antimicrobial active agents. In some embodiments, the composition may include one or more density modifiers and/or thickening agents. In some embodiments, the composition may include any combination of the various components otherwise described herein. Particularly useful hydrogel compositions are those described in the appended Examples in Formulation A4, Formulation I, and/or Formulation I4.

The hydrogel composition in its crosslinked condition preferably can exhibit certain physical characteristics. Preferably, the crosslinked hydrogel composition exhibits excellent adhesion; however, such adhesion preferably is not of a character that prevents ready removal of the composition without harm to the subject. The proper level of adhesion may be characterized in relation to the adhesion peel strength of the applied material. Specifically, the adhesion peel test pull force required for removal of applied, crosslinked hydrogel composition preferably is in the range of about 0.05 Newtons (N) to about 0.5 N, about 0.08 N to about 0.45 N, or about 0.1 N to about 0.4 N. In some embodiments, the adhesion peel test pull force value can be greater than 0.01 N, greater than 0.02 N, or greater than 0.03 N. Likewise, the adhesion peel test pull force value can be less than 1 N, less than 0.8 N, or less than 0.7 N.

A useful hydrogel composition also preferably exhibits a defined swellability. Such character can be evaluated by forming a sample of a crosslinked hydrogel composition, fully dehydrating the sample, and then contacting the fully dehydrated sample with a test liquid (e.g., phosphate buffer solution—PBS). A "fully" dehydrated sample can comprise less than 5% water by weight, less than 2% water by weight, less than 1% water by weight, less than 0.5% water by weight, or less than 0.1% water by weight. The swelling test can be carried out under defined conditions (e.g., a temperature of about 25° C. and a relative humidity of about 60%). Preferably, a fully dehydrated sample of the hydrogel composition has a swelling range of about 100% to about 1000%, about 150% to about 900%, or about 250% to about 750% of the starting weight of the fully dehydrated sample under such conditions.

Delivery of the Compositions

Appropriate viscosity depends upon the delivery means to be employed. Generally, the composition should have a viscosity lower than about 800 cps, preferably lower than 300 cps, more preferably lower than 200 cps to be delivered via aerosol. Delivery through a pump spray generally requires a lower viscosity, such as less than about 150 cps.

Spray without aerosol calls for a viscosity less than about 50 cps. In some embodiments, viscosity of the composition at the time of administration can be about 5 cps to about 750 cps, about 10 cps to about 500 cps, or about 20 cps to about 200 cps.

The hydrogel composition can be delivered during administration via any appropriate means, such as dipping, coating, spraying, injecting, or similar methods. In some embodiments, the hydrogel composition can be delivered from a spray device or a stream device. The spray device, for example, can include a container having a dispenser for spray delivery of the liquid composition. The type of container used is variable, depending upon compatibility with the composition and the spray dispenser and can be glass, plastic, or metal. If the solutions are of a low enough viscosity, a spray delivery may be achieved with simple mechanical forces such as those achieved when depressing the plunger of a syringe by hand through an appropriately designed nozzle.

The composition can also be delivered using a syringe outfitted with a spray head, or a dual spray device outfitted with a spray head and, optionally, a mixing chamber. Generally, any chemical, mechanical or electronic method for propelling the liquid composition as a spray from the container is appropriate. In one embodiment, a compatible liquid or gaseous aerosol propellant is placed in an appropriate container along with the composition and the dispenser includes a valve mechanism that enables atomized spray delivery of the liquid composition.

A device is used having two containers so that the components are kept apart until used. The device can have a single dispenser, such as a spray tip from Nordson Corp. or a device having a double dispenser, e.g. a bar spray tip from Micromedics can be used. If a double dispenser is used, the sprays from the dispensers can be aligned to substantially overlap. A suitable device is described in U.S. Pat. No. 5,989,215, for example. It is also possible, although less preferred, to apply the two solutions sequentially. A mixer may be employed in the case of a single dispenser to mix the two solutions before or during spraying. The device may include a meter so that the quantity of composition can be controlled. In some embodiments, components of the hydrogel composition may be stored separately in individual barrels of a multi-barrel syringe, and the components can be mixed during delivery of the components from the individual barrels (e.g., either in a common passage formed in the syringe or after expression from the syringe. See, for example, devices such as described in U.S. Pat. No. 5,819,988, the disclosure of which is incorporated herein by reference.

Depending upon the means of delivery and the desired treatment, the hydrogel composition can be applied so as to result in a hydrogel coating having a thickness of about 0.01 to 5 mm, about 0.05 to about 4 mm, or about 0.1 to 3 mm. It may be desirable to apply several layers of the composition to the delivery site to achieve the desired amount of coverage.

Examples of devices that could be used, or modified for use, to deliver the compositions include those described in WO 2015/038281 to Zoetis, US 2015/0080841 to Zoetis LLC, U.S. Pat. No. 5,989,215 to Baxter International Inc., U.S. Pat. No. 8,353,877 to Bimeda Research & Development, WO 2003/022245 to Bimeda Research & Development, and WO 2013/021186 to Norbrook Laboratories Limited, the disclosures of which are incorporated herein by reference.

EXAMPLES

The examples below serve to further illustrate the invention, to provide those of ordinary skill in the art with a complete disclosure and description of how the compounds, compositions, articles, devices, and/or methods described herein are made and evaluated, and are not intended to limit the scope of the invention. In the examples, unless expressly stated otherwise, amounts and percentages are by weight, temperature is in degrees Celsius or is at ambient temperature, and pressure is at or near atmospheric. The examples are not intended to restrict the scope of the invention.

Modifications and variations of the present invention will be apparent to those skilled in the art from the forgoing detailed description. All modifications and variations are intended to be encompassed by the present disclosure. All publications, patents, and patent applications cited herein are hereby incorporated by reference in their entirety.

Example 1

Formulations

Hydrogel formulations were prepared from two solutions, an oxidant solution and a reductant solution, which were combined to form the hydrogel. The two solutions contained some ingredients in equal parts (macromer and glycerol) but only the oxidant solution contained hydrogen peroxide and only the reductant solution contained Fe(II), ascorbic acid, and calcium chloride.

The components of the oxidant were mixed into a homogeneous solution. Once fully mixed, the oxidant component was dispensed into one part of a dual barrel syringe. The components of the reductant were similarly mixed into a homogenous solution. After thorough mixing, the reductant component was dispensed into the second part of the dual barrel syringe.

The macromers used in the formulations were PVA of the molecular weights noted, substituted with the noted amounts of N-acrylamidoacetaldehyde dimethyl acetal (NAAADA). The macromers were prepared applying the method of Example 15 from U.S. Pat. No. 5,932,674, and were isolated as aqueous 200 mg/mL solutions for formulation.

| Formulation A | | | |
|---|---|---|---|
| Formulation A-Oxidant solution | | | |
| Formulation | | Final Composition | |
| Component | Weight % | Ingredient | mg/g |
| Macromer 1 solution[a] | 31.0 | Macromer 1 | 60 |
| H$_2$O$_2$ solution[c] | 1.5 | H2O2 | 0.8 |
| Chelant solution[d] | 8.1 | Diethylenetriamine penta(methylene phosphonic acid) | 0.1 |
| Glycerol | 16.0 | Glycerol | 160 |
| Water | 22.7 | Water | qs 1 g |
| Formulation A-Reductant solution | | | |
| Formulation | | Final Composition | |
| Component | Weight % | Ingredient | mg/g |
| Macromer 1 solution[a] | 31.0 | Macromer 1 | 60 |
| Iron/ascorbic acid solution[e] | 13.8 | Ferrous lactate | 1.6 |
| | | Ascorbic acid | 2.2 |

Formulation A (continued)

| Calcium chloride | 10.7 | Calcium chloride | 107 |
| Glycerol | 16.0 | Glycerol | 160 |
| Water | 16.7 | Water | qs 1 g |

[a] Macromer 1 solution: aqueous 200 mg/mL Macromer 1 (Macromer 1: 67 kDa PVA functionalized with 0.1 mmol/g NAAADA)
[c] $H_2O_2$ solution: aqueous 50 mg/mL hydrogen peroxide
[d] Chelant solution: 150 μL Dequest 2060S diluted in water to 100 mL
[e] Aqueous 11 mg/mL ferrous lactate plus 15 mg/mL ascorbic acid

Formulation A4

Formulation A4-Oxidant solution

| Formulation | | Final Composition | |
| --- | --- | --- | --- |
| Component | Weight % | Ingredient | mg/g |
| Macromer 1 solution[a] | 31.0 | Macromer 1 | 60 |
| PVA 3-83 solution[b] | 20.7 | PVA 3-83 | 60 |
| $H_2O_2$ solution[c] | 1.5 | H2O2 | 0.8 |
| Chelant solution[d] | 8.1 | Diethylenetriamine penta(methylene phosphonic acid) | 0.1 |
| Glycerol | 16.0 | Glycerol | 160 |
| Water | 22.7 | Water | qs 1 g |

Formulation A4-Reductant solution

| Formulation | | Final Composition | |
| --- | --- | --- | --- |
| Component | Weight % | Ingredient | mg/g |
| Macromer 1 solution[a] | 31.0 | Macromer 1 | 60 |
| PVA 3-83 solution[b] | 13.3 | PVA 3-83 | 40 |
| Iron/ascorbic acid solution[e] | 13.8 | Ferrous lactate | 1.6 |
| | | Ascorbic acid | 2.2 |
| Calcium chloride | 10.7 | Calcium chloride | 107 |
| Glycerol | 16.0 | Glycerol | 160 |
| Water | 16.7 | Water | qs 1 g |

[a] Macromer 1 solution: aqueous 200 mg/mL Macromer 1 (Macromer 1: 67 kDa PVA functionalized with 0.1 mmol/g NAAADA)
[b] PVA 3-83 solution: aqueous 300 mg/mL PVA 3-83
[c] $H_2O_2$ solution: aqueous 50 mg/mL hydrogen peroxide
[d] Chelant solution: 150 μL Dequest 2060S diluted in water to 100 mL
[e] Aqueous 11 mg/mL ferrous lactate plus 15 mg/mL ascorbic acid

Formulation I

Formulation I-Oxidant solution

| Formulation | | Final Composition | |
| --- | --- | --- | --- |
| Component | Weight % | Ingredient | mg/g |
| Macromer 2 solution[a] | 34.0 | Macromer 2 | 60 |
| PVA 3-83 solution[b] | 0.0 | PVA 3-83 | 0 |
| $H_2O_2$ solution[c] | 1.5 | H2O2 | 0.8 |
| Chelant solution[d] | 8.3 | Diethylenetriamine penta(methylene phosphonic acid) | 0.1 |
| Glycerol | 16.0 | Glycerol | 160 |
| Water | 40.4 | Water | qs 1 g |

Formulation I-Reductant solution

| Formulation | | Final Composition | |
| --- | --- | --- | --- |
| Component | Weight % | Ingredient | mg/g |
| Macromer 2 solution[a] | 34.0 | Macromer 2 | 60 |
| PVA 3-83 solution[b] | 0.0 | PVA 3-83 | 0 |
| Iron/ascorbic acid solution[e] | 13.8 | Ferrous lactate | 1.6 |
| | | Ascorbic acid | 2.2 |
| Calcium chloride | 10.7 | Calcium chloride | 107 |
| Glycerol | 16.0 | Glycerol | 160 |
| Water | 25.5 | Water | qs 1 g |

[a] Macromer 2 solution: aqueous 200 mg/mL Macromer 2 (Macromer 2: 130 kDa PVA functionalized with 0.1 mmol/g NAAADA)
[b] PVA 3-83 solution: aqueous 300 mg/mL PVA 3-83
[c] $H_2O_2$ solution: aqueous 50 mg/mL hydrogen peroxide
[d] Chelant solution: 150 μL Dequest 2060S diluted in water to 100 mL
[e] Aqueous 11 mg/mL ferrous lactate plus 15 mg/mL ascorbic acid

Formulation I4

Formulation I4-Oxidant solution

| Formulation | | Final Composition | |
| --- | --- | --- | --- |
| Component | Weight % | Ingredient | mg/g |
| Macromer 2 solution[a] | 26.7 | Macromer 2 | 47 |
| PVA 3-83 solution[b] | 16.7 | PVA 3-83 | 50 |
| $H_2O_2$ solution[c] | 1.5 | H2O2 | 0.8 |
| Chelant solution[d] | 8.1 | Diethylenetriamine penta(methylene phosphonic acid) | 0.1 |
| Glycerol | 16.0 | Glycerol | 160 |
| Water | 31.1 | Water | qs 1 g |

Formulation I4-Reductant solution

| Formulation | | Final Composition | |
| --- | --- | --- | --- |
| Component | Weight % | Ingredient | mg/g |
| Macromer 2 solution[a] | 26.7 | Macromer 2 | 50 |
| PVA 3-83 solution[b] | 16.7 | PVA 3-83 | 50 |
| Iron/ascorbic acid solution[e] | 13.3 | Ferrous lactate | 1.6 |
| | | Ascorbic acid | 2.0 |
| Calcium chloride | 10.7 | Calcium chloride | 107 |
| Glycerol | 16.0 | Glycerol | 160 |
| Water | 16.7 | Water | qs 1 g |

[a] Macromer 2 solution: aqueous 200 mg/mL Macromer 2 (Macromer 2: 130 kDa PVA functionalized with 0.1 mmol/g NAAADA)
[b] PVA 3-83 solution: aqueous 300 mg/mL PVA 3-83
[c] $H_2O_2$ solution: aqueous 50 mg/mL hydrogen peroxide
[d] Chelant solution: 150 μL, Dequest 2060S diluted in water to 100 mL
[e] Aqueous 11 mg/mL ferrous lactate plus 15 mg/mL ascorbic acid Example 2

Swelling and Adhesion Testing

For adhesion testing, samples were conditioned at 37° C. for 2 hrs prior to testing. Adhesion data were generated between 0 to 2 hours after in situ formation of the hydrogel composition. The swelling values provided herein were read after 72 hours of swelling time. Swelling to the recorded values occurred during the noted time frame, and it is understood that readings taken between in situ formation and the final reading time would have been less than the value recorded at 72 hours.

For adhesion testing, peel test samples were made using a 60 mm×50 mm×3 mm mold attached to damp (or wet) collagen with an affixed gauze backing to facilitate the peeling. To assess adhesion on these samples, a modified procedure from the standard 180° peel test was performed with the principal modification of setting the sample horizontally as opposed to vertically. A high-precision universal peel tester was used to measure the force to pull the backing "on itself". The pulling was done at a constant speed, and a plot of force over time of peel was generated. The reporting force is the maximum recorded force during the pulling of the gauze+sample from the wet, affixed collagen backing. Results are shown in FIG. 2.

For the swell testing, cylindrical preformed gel samples were prepared by slowly administering the macromer to ensure no bubbles into a 6 cm×0.5 cm piece of rigid plastic tubing. The formed hydrogel was extracted from the tubing and samples used were between 1-2 g.

Test Method (Dehydration): Prepared samples were first dehydrated by placing in oven at 45° C. over a period of time until there was no significant weight change. Sample weights were taken at time 0 and then again every 24 hours until full dehydration was achieved.

Test Method (Swelling): Fully dehydrated samples were placed in sealed test tubes containing 15 mL PBS solution at 25° C., 60% RH and allowed to swell. Sample weight of the fully dehydrated sample is considered time 0 in this case. Sample weights were taken at time 0, 1 hr, 2 hr, 24 hr, 48 hr, 72 hr, and 7 days.

Adhesion and swelling testing results are shown in FIGS. 2 and 3, respectively. Referring to FIG. 2, samples A7, A8, I, A, I4, and A4 have PVA content between 4.5 and 9.0% by weight, and glycerol content between 5% and 16% by weight. Samples A7, A8, I, A, and I4 exhibit adhesion range from 0.07N to 0.35 N. Referring to FIG. 3, samples A8, I, A, I4, and A4 swelled 400 to 600% after 72 hours. The samples depicted in FIGS. 2 and 3 are summarized below.

| Formulation | PVA Mol. Wt. | % PVA | % Glycerol | Filler |
| --- | --- | --- | --- | --- |
| A6 | 67 kDa | 6.00 | 0.0 | None |
| I9 | 130 kDa | 6.02 | 23.0 | None |
| A9 | 67 kDa | 6.03 | 25.0 | None |
| A7 | 67 kDa | 6.03 | 5.0 | None |
| A8 | 67 kDa | 6.03 | 10.0 | None |
| I | 130 kDa | 6.02 | 16.0 | None |
| A | 67 kDa | 6.03 | 16.0 | None |
| I4 | 130 kDa | 4.73 | 16.0 | 5% of aqueous 30% 3-83 Filler |
| A4 | 67 kDa | 6.03 | 16.0 | 5% of aqueous 30% 3-83 Filler |

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation. Unless otherwise indicated, percentages for components of compositions disclosed herein are on a percent by weight basis.

The invention claimed is:

1. A method of treating an animal, the method comprising:
   providing a hydrogel composition configured for in situ polymerization, said composition comprising:
      a first solution comprising an oxidant and an oxidant stabilizer; and
      a second solution comprising a reductant and a reductant stabilizer;
   wherein one or both of the first solution and the second solution includes a water soluble polyvinyl alcohol macromer having an added functional group so as to be configured for in situ polymerization, and one or both of the first solution and the second solution includes a polyol; and
   administering the first solution and the second solution to mammary tissue of the animal such that in situ polymerization of the hydrogel composition occurs via the added functional group.

2. The method of claim 1, wherein the hydrogel composition is administered one or both of externally or internally to the mammary tissue.

3. The method of claim 1, wherein the hydrogel composition is administered to a teat of the animal or to a plurality of teats of the animal.

4. The method claim 3, wherein the hydrogel composition is administered to an external surface of the teat or teats.

5. The method of claim 3, wherein the hydrogel composition is infused into the teat or teats.

6. The method of claim 3, wherein the hydrogel composition is administered to the animal in an amount of about 0.5 g to about 5.0 g per teat.

7. The method of claim 1, wherein the animal is a livestock animal.

8. The method of claim 1, wherein the animal is a heifer or cow.

9. The method of claim 8, wherein the hydrogel composition is administered during a transition period that extends through a dry period of the heifer or cow.

10. The method of claim 1, wherein the hydrogel composition has an adhesion peel test pull force value of about 0.05 N to about 0.5 N.

11. The method of claim 1, wherein the hydrogel composition is configured such that a fully dehydrated sample of the hydrogel composition has a swelling range of about 100% to about 1000% of starting weight of the fully dehydrated sample when combined with a PBS solution at a temperature of about 25° C. and a relative humidity of about 60%.

12. The method of claim 1, wherein the hydrogel composition is Formulation A4, Formulation I, or Formulation I4.

13. The method of claim 1, further comprising administering an antimicrobial agent to the mammary tissue of the animal.

14. The method of claim 13, wherein the antimicrobial agent is ceftiofur hydrochloride.

15. The method of claim 1, wherein said administering is effective for treating or preventing a microbial infection in the mammary tissue of the animal.

16. The method of claim 15, wherein the microbial infection is mastitis.

17. The method of claim 16, wherein treating or preventing the microbial infection comprises treating or preventing a bacterial invasion of the mammary tissue.

18. The method of claim 1, wherein the method comprises forming a physical barrier in a teat canal of the animal, said physical barrier being effective for prophylactic treatment of mammary disorders.

19. The method of claim 1, wherein said treatment is effective such that milk obtained from the animal during said treatment is suitable for use in the production of a milk product.

20. The method of claim 19, wherein the milk product is one or more of dry milk, liquid milk, yogurt, or cheese.

21. The method of claim 1, wherein the hydrogel composition is administered during a postpartum period of a non-lactating animal.

22. The method of claim 1, wherein the hydrogel composition is administered during a pre-partum period of the animal.

23. The method of claim 1, wherein the hydrogel composition is administered to a healthy animal exhibiting no symptoms of an infection of the mammary tissue.

24. The method of claim 1, wherein said treatment is effective to reduce the period of time during which milk obtained from the animal must be withheld from use in the production of a milk product.

25. The method of claim 24, wherein said treatment is effective to reduce the period of time during which milk obtained from an animal being prophylactically treated for mastitis must be withheld from use in the production of a milk product.

26. The method of claim 1, wherein the hydrogel composition is adapted to act as a teat sealant in the treated animal.

27. The method of claim 1, wherein the hydrogel composition further comprises a crosslinking initiator.

* * * * *